US009222879B2

(12) United States Patent
Hartrumpf

(10) Patent No.: US 9,222,879 B2
(45) Date of Patent: Dec. 29, 2015

(54) APPARATUS AND METHOD FOR OPTICALLY CHARACTERIZING MATERIALS

(75) Inventor: Matthias Hartrumpf, Karlsruhe (DE)

(73) Assignee: Fraunhofer-Gesellschaft zur Förderung der angewandten Forschung e.V. (DE)

(*) Notice: Subject to any disclaimer, the term of this patent is extended or adjusted under 35 U.S.C. 154(b) by 119 days.

(21) Appl. No.: 13/818,188

(22) PCT Filed: Sep. 9, 2011

(86) PCT No.: PCT/EP2011/004553
§ 371 (c)(1),
(2), (4) Date: May 6, 2013

(87) PCT Pub. No.: WO2012/038036
PCT Pub. Date: Mar. 29, 2012

(65) Prior Publication Data
US 2013/0222803 A1 Aug. 29, 2013

(30) Foreign Application Priority Data
Sep. 24, 2010 (DE) .................... 10 2010 046 438

(51) Int. Cl.
G01N 21/21 (2006.01)
G01N 15/14 (2006.01)

(52) U.S. Cl.
CPC ............ G01N 21/21 (2013.01); G01N 15/1434 (2013.01); G01N 15/1463 (2013.01)

(58) Field of Classification Search
CPC ............ G01N 21/21; G01N 15/1434; G01N 15/1463; G01N 15/1459
USPC ........................................ 356/369
See application file for complete search history.

(56) References Cited

U.S. PATENT DOCUMENTS 5,442,446 A * 8/1995 Gerber et al. ................. 356/428
6,097,491 A * 8/2000 Hartrumpf .................... 356/622
(Continued)

FOREIGN PATENT DOCUMENTS

AT 380814 B 7/1986
DE 4317513 A1 12/1994
(Continued)

OTHER PUBLICATIONS

"International Application No. PCT/EP2011/004553, International Preliminary Report on Patentability mailed Apr. 4, 2013", (English Translation), 13 pgs.
(Continued)

Primary Examiner — Michael A Lyons
Assistant Examiner — Violeta A Prieto
(74) Attorney, Agent, or Firm — Schwegman Lundberg & Woessner, P.A.

(57) ABSTRACT

The present invention relates to a device for optical characterization of a sample and/or of the material(s) of the same having an illumination unit that can be orientated to illuminate with incident light a sample spatial portion into which the sample can be introduced, a detection unit which is orientated or can be orientated to image the sample introduced into the sample spatial portion by receiving light reflected by the sample, and which is configured to detect at least two different, preferably orthogonal, polarization components in the reflected light, and an evaluation unit with which, in the imaging data recorded by the detection unit, those imaged surface elements (reflection elements) of the sample can be identified, and with which the detected different polarization components for these reflection elements can be evaluated for optical characterization.

3 Claims, 9 Drawing Sheets

(56) References Cited

U.S. PATENT DOCUMENTS

Figures 1A, 1B:
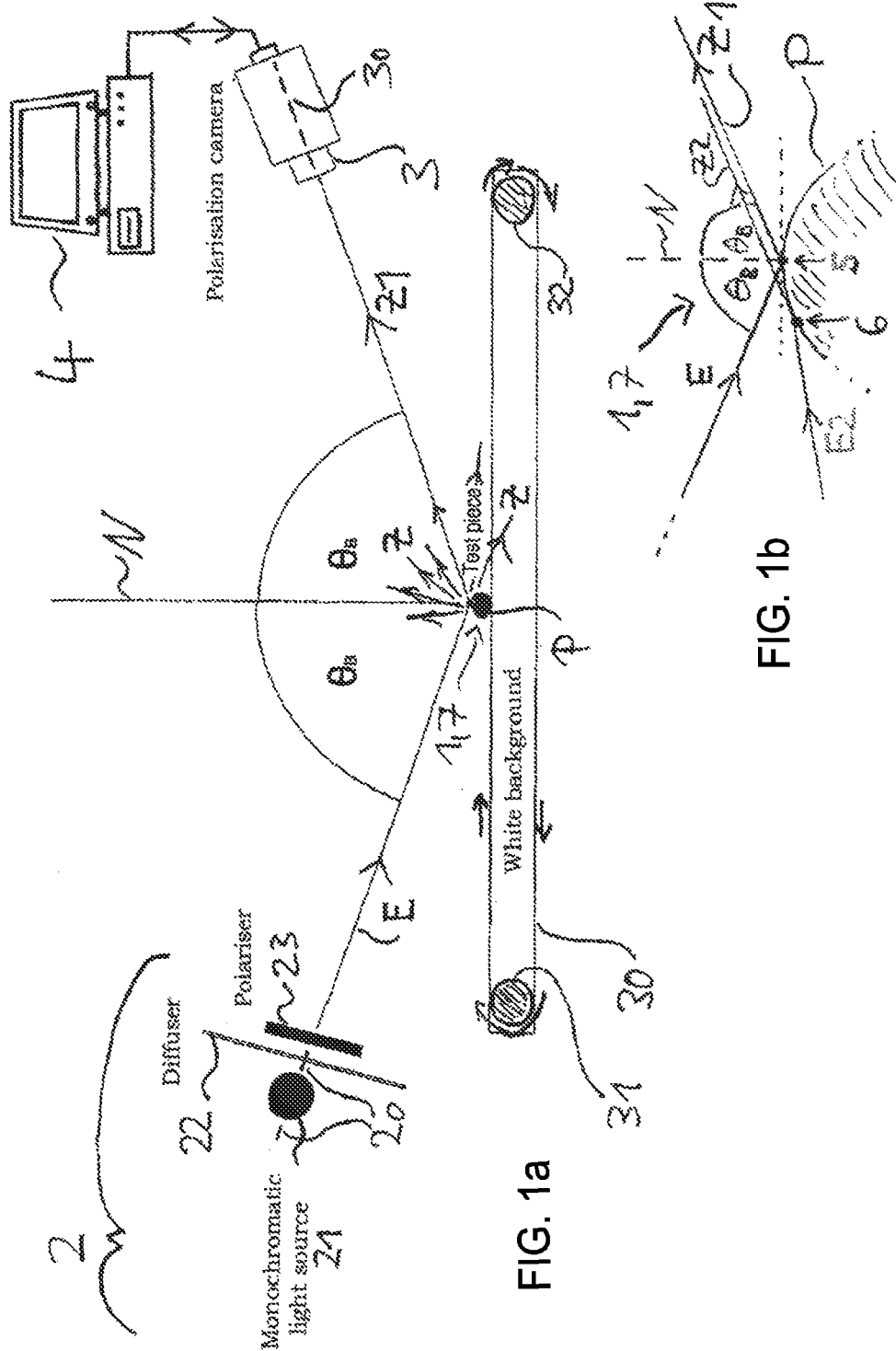

| | | | |
|---|---|---|---|
| 7,612,880 B2* | 11/2009 | Chipman | 356/364 |
| 7,768,643 B1 | 8/2010 | Janssens et al. | |
| 2004/0169850 A1* | 9/2004 | Meeks | 356/237.2 |
| 2009/0103094 A1* | 4/2009 | Hilfiker et al. | 356/369 |
| 2010/0012031 A1* | 1/2010 | Torregrosa et al. | 118/712 |
| 2010/0230327 A1* | 9/2010 | Hartrumpf et al. | 209/577 |
| 2010/0280765 A1* | 11/2010 | Marquardt et al. | 702/24 |

FOREIGN PATENT DOCUMENTS

| | | |
|---|---|---|
| DE | 102007062052 A1 | 6/2009 |
| WO | WO-2009/030004 A1 | 3/2009 |
| WO | WO-2009/049594 A1 | 4/2009 |
| WO | WO-2009/064626 A1 | 5/2009 |

OTHER PUBLICATIONS

"International Application No. PCT/EP2011/004553, Written Opinion mailed Jan. 16, 2012", (English Translation), 11 pgs.

"International Application No. PCT/EP2011/004553, International Search Report and Written Opinion mailed Jan. 16, 2012", (Jan. 16, 2012), 17 pgs.

* cited by examiner

Resulting image (blue channel divided by sum of blue channel and red channel)

Threshold 181, thick 8

APPARATUS AND METHOD FOR OPTICALLY CHARACTERIZING MATERIALS

PRIORITY CLAIM TO RELATED APPLICATIONS

This application is a national stage application under 35 U.S.C. §371 of PCT/EP2011/004553, filed Sep. 9, 2011, and published as WO 2012/038036 A1 on Mar. 29, 2012, which claims priority to German Application No. 10 2010 046 438.4, filed Sep. 24, 2010, which applications and publication are incorporated by reference as if reproduced herein and made a part hereof in their entirety, and the benefit of priority of each of which is claimed herein.

The present invention relates to a device and a method for optical characterisation of a sample and/or of the material (or the materials) of the same. The characterisation is thereby effected on the basis of evaluation of the polarisation of light which is radiated onto the sample and reflected by the sample. The device and the method can be used in particular for surface inspection or also for sorting bulk material by evaluation of the polarisation of the reflected light.

Methods for optical characterisation of samples based on reflectometry or ellipsometry are already known from the state of the art. See for example Thomas Geiler "Polarisationsbildgebung in der industriellen Qualitatskontrolle" (Polarisation imaging in industrial quality control), VDM Press, August 2008. Devices for classification of samples in the form of bulk material are also known from the state of the art (WO 2009/049594 A) which operate on the basis of light which is reflected on a retroreflector, which can be polarisation-selective, and detected with respect to its various polarisation components.

However, all these implementations demand either a planar surface of the test pieces or a time-consuming, simultaneous variation of the angle of incidence and of reflection is implemented. In addition, also a variation in the polarisation of the illumination is often implemented.

It is the object of the present invention to develop devices and methods for optical characterisation of samples, in particular devices (and corresponding methods) based on the technology of reflectometry or ellipsometry and polarimetry respectively such that the samples (in particular also non-planar samples or test pieces, e.g. in the form of bulk materials) can be characterised easily and reliably with respect to their material/materials. It is also the object in particular to configure the devices and the corresponding methods such that this characterisation can be effected rapidly (in the range of a few ¹/₁₀ seconds up to a few seconds), i.e. in step with the production of samples (in-line) or with a bulk material flow.

This object is achieved by a device according to claim 1, by a device according to claim 12 and by a method according to claim 14. Advantageous embodiments of the devices according to the invention and of the method according to the invention can be deduced respectively from the dependent patent claims.

In the following, the present invention is described firstly in general, then in detail with reference to various embodiments. The individual features of the invention which are described in the embodiments and produced in combination with each other need not thereby be produced precisely in the feature combination shown in the respective embodiment within the scope of the invention, but rather can also be produced in different combinations with each other. In particular, some of the illustrated features can also be omitted or combined in different ways with further illustrated individual features of the embodiments.

The present invention, as described subsequently, uses as basis the technologies of reflectometry or of ellipsometry which are known to the person skilled in the art. The corresponding bases are known for example in H. G. Tompkins, W. A. McGahan "Spectroscopic Ellipsometry and Reflectometry", Wiley Interscience, 1999 or in M. Faupel "Abbildende Ellipsometrie und ihre Anwendung" (Imaging ellipsometry and application thereof), VDI reports no. 1996: Optische Messung technischer Oberflächen in der Praxis (Optical measurement of technical surfaces in practice); 2007 and are therefore not described in detail in the following.

A basic idea of the present invention is based on identifying, for those surface elements of the sample which reflect light radiated onto the sample into a detection unit configured for detecting the light, and on detecting and evaluating, for these surface elements of the sample (subsequently also termed reflection elements), different polarisation components of the reflected light. The sample is illuminated for this purpose with preferably monochromatic light. (Monochromatic light is not absolutely necessary but in general is better suited for example in the case of samples with dispersion). Alternatively hereto or in combination therewith, it is likewise possible according to the invention to use monochromatic, coherent radiation (laser light) for illumination of the sample and, by means of suitable configuration of the detection unit which receives the beam components reflected on the sample, to calculate all four Stokes' parameters and to use them for characterisation of the light reflected on the sample (and hence for characterisation of the sample itself). In every case, at least two different (preferably: orthogonal) polarisation components in the reflected light are hence detected. (Alternatively to the term of polarisation component, also the term of "polarisation state" is used subsequently within the scope of the invention although, strictly speaking, light can have merely one polarisation state; however, it is clear to the person skilled in the art with the help of the description respectively, what is intended.)

Within the scope of the subsequently described invention, there is thereby understood by the term of light reflected by the sample, all that light emanating from the sample, which is received finally by means of the device according to the invention and can be used for evaluation. The reflected light hence generally concerns the sum of different light components, namely in particular light components scattered on the sample, light components reflected diffusely on the sample and light components reflected reflectively on the sample. (Reflected light therefore relates precisely to those light components which reach the detection unit and not to those light components which arrive back at the illumination unit.) Subsequently, the light reaching the detection unit due to a reflective reflection is termed also reflected light in short: this light hence relates to light of those surface elements of the sample which reflect the light radiated onto the sample into the detection unit whilst fulfilling the reflection condition.

A device according to the invention for optical characterisation of a sample (or of one or more materials of the same) can hence comprise the following elements: firstly an illumination unit which is orientated to illuminate the sample (the illumination unit can also be directed towards a spatial portion of the sample or a spatial volume into which the sample is introduced for illumination). This device comprises in addition a detection unit which is configured to detect a plurality of different (preferably: orthogonal) polarisation components. The detection unit is orientated such that light components, reflected by the sample, of the light radiated onto the sample can be detected. Finally, this device according to the invention comprises an evaluation unit. This can be produced for example as a computer program in a personal computer. However, it is likewise conceivable to configure the evaluation unit as part of the detection unit (e.g. as evaluation program integrated in a camera). In the imaging data recorded by the detection unit (this device according to the invention is hence configured for planar optical imaging of the sample or of a sample portion), those imaged surface elements of the sample, the reflected light of which, received in the detection unit, is based on a reflection of the incident light on the sample, can be identified with this evaluation unit. These surface elements of the sample are subsequently also termed reflection elements, in contrast to those surface elements of the sample which, because of physical effects other than a reflection (e.g. i.e. by light scattering) reflect light into the aperture of the detection unit. The evaluation unit of this device according to the invention is finally configured such that the detected different polarisation components can be evaluated precisely for the reflection elements in order to obtain the desired optical characterisation of the sample. On the basis of this evaluation, it is then possible for example to separate, with this device according to the invention, objects or object regions which have a narrowly tolerated range of optical material constants from objects with deviating optical material constants (sorting device) or to examine the maintenance of optical material constants automatically, e.g. in one production process. Sorting of bulk material is possible in particular with the device according to the invention.

An essential feature of the above-described solution according to the invention (device or also method for optical characterisation using such a device) is hence that, provided it is desired, e.g. by using an evaluation unit with a corresponding computing capacity, also in step with a production or even with a bulk material flow, a plurality of different (e.g. two orthogonal) polarisation components in the light reflected by the sample can be determined for precisely those surface elements of the sample, the normal of which bisects the angle between illumination unit and detection unit, and which therefore represent the reflection elements of the surface of the sample. Automatic detection, as to whether a specific surface element (i.e. an observed object point) is a reflection element, i.e. fulfils the above-mentioned reflection condition for orientation of its surface normal, can be effected, as described subsequently in more detail, for example by an intensity test of the intensity which is reflected or detected in total by the imaged surface element.

Within the scope of the present invention, an individual physical object is not necessarily understood by a sample, a sample can quite generally also concern a flow of many individual, moving objects of different materials (i.e. a sample flow within the scope of a bulk material to be sorted or to be characterised, i.e. a bulk material flow). As described subsequently in more detail with reference to concrete examples, an illumination unit used within the scope of the invention need not necessarily concern an individual light source, rather also in parallel a plurality of suitably disposed light sources which illuminate one and the same sample can be used. In general, the reflection condition is then fulfilled for each of the light sources used. Within the scope of the present invention, there is understood by reflected light, all those light components which originate in light components, radiated by the illumination unit and incident on the sample, and which are not absorbed by the sample, but which again leave the sample or the surface thereof—generally in a different direction from the direction of incidence—by means of any processes (reflection, scattering, . . . ) and hence can be detected outside the sample.

An essential idea of the above-described device according to the invention is hence to detect and evaluate only the beam components reflected on the sample (reflectively), i.e. to evaluate only different polarisation states for the thus reflected beam components for characterisation of the sample, but not for the other reflected, e.g. scattered, beam components. As described subsequently in more detail, it is thereby particularly advantageous to dispose the illumination unit and the detection unit at the Brewster angle provided that the characterisation task, when using the device according to the invention, resides precisely in detecting the presence of a defined material or in identifying individual elements of this defined material in a sample comprising a large number of objects of different materials (the Brewster angle adjusted in the device is then the Brewster angle of this material). This arrangement at the Brewster angle is advantageous in particular for the reason that the beam components reflected on samples or sample elements of this material have merely one polarisation direction so that the material characterisation is possible in a particularly simple manner. An arrangement at the Brewster angle is however not absolutely necessary since the different polarisation components for the reflection elements on the surface of the sample can also be evaluated without maintaining this special reflection condition (e.g. a differentiation can be made with respect to the incident intensities thereof).

In a first advantageous embodiment of the above-described device according to the invention, the evaluation unit is configured such that firstly the reflection elements can be identified in the recorded imaging data before the detected different polarisation components can be evaluated for these (or based on these) identified reflection elements. For example, the reflection elements can be established with reference to an evaluation of the total detected intensities of the individual surface elements (or of the image pixels of the images detected by the detection unit) by those surface elements being identified as reflection elements, the total intensity of which (sum of the intensities of all the detected polarisation components) lies above a fixed threshold value (e.g. that intensity value, above which the intensity of 20% of all the imaged surface elements lies, can be defined as threshold value). Then the different (e.g. orthogonal) polarisation components are evaluated merely for the thus identified reflection elements, e.g. viewed separately or viewed with respect to the intensity ratios thereof.

As an alternative thereto, it is also possible, in the recorded imaging data for all imaged surface elements (these comprising both imaged surface elements of the sample and imaged surface elements of structures which do not belong to the sample but are nevertheless imaged), to consider firstly the detected different polarisation components, e.g. separately or according to the ratios thereof, and (for example by setting a threshold value) to evaluate them in order to determine those surface elements of the sample which are reflection elements. Thus for example all surface elements, the intensity of which exceeds a predetermined threshold value for a defined polarisation component in the imaging data, can be defined as reflection elements. For the reflection elements thus identified by means of the different polarisation components, the different polarisation components are then evaluated further (for example by forming a ratio of the intensities in imaging data or polarisation partial images which correspond to different polarisation components and are recorded by the detection unit) in order to implement the optical characterisation of the sample.

In an advantageous embodiment, the device according to the invention is configured such that the differentiation, required for identifying the reflection elements, of reflection elements and of surface elements, the reflected, received light of which is not based on a reflection of the incident light on the sample (scattered elements), is effected on the basis of the intensity or of the intensities of imaging data of one, of a plurality or of all of the detected polarisation components. In particular, intensity differences or also intensity ratios of the different detected polarisation components can be used for determination of the reflection elements. It is also possible to use the total intensity of all polarisation components, detected by the detection unit, of the light arriving for imaging for identification of the reflection elements. Thus for example, those surface elements, the associated imaging values of which, in the images detected by the detection unit, are in total above a predefined threshold value, can be identified as reflection elements. Such a threshold value can be defined for example as 90%/10% threshold value, i.e. it can by means of this be established that 90% of the total intensity values of all imaged surface elements are below this threshold value and 10% above.

As an alternative thereto or also in combination with the intensity-based identification of the reflection elements, the reflection elements can also by defined on the basis of the position thereof in images of the sample produced corresponding to the different polarisation components (or also corresponding to the received total intensity): for this purpose, the position of the surface elements (e.g. taking into account the intensities thereof) can be evaluated relative to each other and/or relative to one or more reference point(s) in the images of the sample. In particular centres or edge points of images of the sample can serve as reference points. For example, by suitable configuration of the sample background or by additional illumination (which ensures a constant, low background intensity), individual elements of the sample (e.g. bulk material particles) can be differentiated from the background by for example the change in intensity at the edge of these sample elements being detected (evaluation of gradients in the image). As an additional condition, that an observed surface element is a reflection element of the sample, it can then be established—in addition to the above-described threshold value setting—that the reflection elements must be located within the thus detected outlines of individual sample elements.

In contrast thereto, those surface elements, the intensity or brightness of which lies below the above-described, adjustable threshold, are then not reflection elements but scattered elements. Also surface elements which are situated outside the sample element limits, which can be identified as described above, are not reflection elements of the sample. Further evaluation of these surface elements is therefore not sensible.

In a further advantageous embodiment of the above-described device according to the invention, evaluation of the identified reflection elements is effected for the purpose of optical characterisation of the sample as follows: a ratio is formed from different polarisation components, which are recorded by the detection unit for the identified reflection elements (e.g. from two linear polarisation components which are orthogonal to each other). This can take place for example by the intensity value, for all the surface elements which were identified as reflection elements, in the image recorded for a first polarisation component, being divided by the intensity value of the corresponding reflection element in the image recorded for a second, different (e.g. orthogonal) polarisation component.

If the thus formed ratio then exceeds or falls below a specific value for a specific minimum number of reflection elements (relative to the total number of surface elements and/or of reflection elements), then information about the presence or absence of a defined material in the sample can hence be obtained: if for example, as reflection condition for the reflection elements, the angle between the optical axis of the detection unit, on the one hand, and the optical axis of the illumination unit, on the other hand, in the triangle which is spanned by the detection unit, the illumination unit and the sample, is adjusted to twice the Brewster angle of a sought material (the reflection elements are then those surface elements of the sample, the normal of which bisects the angle between the two above-mentioned axes), then all those reflection elements which can be assigned to the sought material reflect light components which are polarised merely parallel to the surface of the sample but not light components with a polarisation direction perpendicular thereto. However, this can be detected via setting a corresponding threshold value for the ratio calculated as described above, so that a differentiation of sample elements of the sought material from sample elements made of a different material is possible.

According to the invention, it is hence possible to test whether the ratio of intensities of different polarisation components is within a certain range in order to differentiate defined materials from other materials. In particular in the case of bulk material flows as samples, also the absolute number of those image points or surface elements in the imaging data, which are recorded by the detection unit and for which the ratio calculated as described above exceeds or fall below a threshold value, can thereby be used as sorting criterion. Alternatively thereto, it is possible to evaluate not the absolute number of such surface elements but the relative number of these surface elements in comparison with those surface elements which do not fulfil the threshold value criterion.

In the above-described embodiment variants of the invention, the consideration is crucial that, even with irregular surfaces of samples (e.g. of bulk materials), there is at least one point in the case of each object or element of the sample, i.e. a surface element, which fulfils the reflection condition and with which the object can hence be characterised.

It is particularly advantageous, within the scope of the invention, to make use of surface elements or reflection elements from different directions at the same time or also in succession for the evaluation. Thus of course it basically suffices that the illumination unit used has merely a single illumination element (e.g. a single monochromatic light source, see subsequent embodiment 1).

However, the illumination unit can also comprise a plurality of individual illumination elements which are configured to illuminate the sample with incident light from different directions. The angle between the detection unit or the optical axis thereof, on the one hand, and the respective illumination element or the optical axis thereof, on the other hand, in the triangle which is spanned by the detection unit, the corresponding illumination element and the sample can thereby be identical in all illumination elements. Advantageously, two or four individual illumination elements can be used. The illumination elements can be disposed on the side of the sample situated opposite the detection unit and in a plane orientated preferably perpendicular to the optical axis of the detection unit.

In particular, the individual illumination elements can be disposed at equidistant angle spacings on a circle about the optical axis of the detection unit in this plane. For example, when using four illumination elements, these can thus be disposed at angle spacings of 90° on a circle about the optical axis of the detection unit. For all these illumination elements, the angle ratios described above for the illumination unit (e.g. adjustment to a Brewster angle for a defined material) can then be maintained.

All the devices for optical characterisation described within the scope of the present invention can be configured by suitable provision of further components (e.g. sample storage units etc.) for surface testing of planar coatings as sample.

However it is likewise possible to develop the devices for characterisation, differentiation and/or separation of individual elements of a sample comprising a large number of elements (in particular: bulk material flow). This can take place for example by the illumination unit and the detection unit being disposed for illumination and imaging of a free falling stretch part, e.g. below a vibrator for bulk material. As an alternative thereto, of course, also conveyer belt portions on which bulk material is transported can be illuminated by the illumination unit and scanned by the detection unit. The last-mentioned devices can then be configured in particular also for sorting sample elements which deviate from one or more predefined material parameter(s) (which is/are determined for optical characterisation by evaluation of the reflection elements).

The above-described devices according to the invention can be configured as a laser scanner system with an illumination unit which scans one- or two-dimensionally the sample or sample spatial portion in which this sample is disposed, on the basis of one or more laser(s) and with one or more suitable receiving unit(s) as detection unit.

As a alternative thereto, it is however also possible to use one or more monochromatic light sources as illumination unit or illumination element(s). As detection unit, one or more camera(s), in particular polarisation camera(s) and/or CCD-based camera(s), can then be used.

Illumination of the sample is effected advantageously with one or more defined wavelength(s) in the visible range; it is however basically also conceivable to use for example infrared radiation for the illumination provided that the receiving units are then correspondingly adapted.

Subsequently, a few concrete embodiments of the illumination unit-detection unit system of the present invention are now described:

Thus, a camera which is used in a reflection arrangement, as described above, and with which for example two orthogonal polarisation components can be detected for example for each scanned surface element, can be a camera consisting of two individual cameras. In the beam path in front of the individual cameras, a polarising optical element (e.g. prism or beam splitter) is disposed, with which the light reflected by the sample can be split into two different polarisation components. The light of the one polarisation component is then directed by the polarising optical element towards the one individual camera, the light of the other polarisation component towards the other of the two individual cameras. It is thereby advantageous to provide a pixel adaptation in order to coordinate the position of the detected reflection elements in the images of both individual cameras.

As a alternative thereto, a multiline camera can be provided, a number of polarisers which corresponds to the number of lines of the camera being provided in the beam path in front of this camera. Two (or more, e.g. six) different types of polarisers, for example two polarisers orientated orthogonally relative to each other (in the case of six polarisers, e.g. 0°, 45°, 90°, 135°, left-circular and right-circular polarising polarisations) thereby exist. The two or more polarisation directions are detected by the camera: in front of the individual lines of the camera, polarisers of the one type and of the other type, in the case of two different polarisers, are disposed alternately so that light of a first polarisation component and of a second polarisation component, e.g. orthogonal to the first polarisation component, is imaged respectively alternately onto the camera lines. In the case of for example six different polarisers, accordingly six adjacent lines for the six different types are required.

As an alternative thereto, a camera which, in the beam path in front of its sensor chip, comprises a polarisation strip filter or a polarisation mosaic filter can be used. Such a filter splits the light reflected by the sample into the different polarisation components which then are directed, in lines or corresponding to the mosaic arrangement of the filter, towards the respective sensor cells of the camera chip (which sensor cells of the chip receive light of which polarisation component is known on the basis of the already known filter shape so that the evaluation can be correspondingly effected).

It is likewise conceivable to provide a plurality of differently polarised illumination sub-units (e.g. individual lamps) which are all orientated to illuminate the sample with incident light. The individual illumination sub-units are switched on and off again temporally in succession, therefore illuminate the sample respectively in succession for a predefined time duration. The individual polarisation components are then detected during different, precisely defined time intervals respectively by the total camera surface of a non-polarisation-sensitive camera (preferably a multiline camera is used), hence the differently polarised illuminations are quasi-flashed. If the device is used with moving samples (bulk material flow), the flashing frequency or the frequency of the switch-over between the individual illumination sub-units must be synchronised advantageously with the sample speed.

This synchronisation has the following advantage: in general, the sample is in motion during the scanning (e.g. on a corresponding falling stretch or also flight stretch in the case of a for example parabolic discharge from a conveyer belt, i.e. the image of the sample is moved, in the case of the individual camera images taken temporally in succession for evaluation, within these camera images, i.e. changes its position in the individual camera images. Since now however generally both (or the more than two) polarisation states are required from one and the same point or surface element of the sample, it must in general be known how far the sample has moved between two adjacent camera images in order also to detect and evaluate in fact the polarisation states of one and the same surface element of the sample (it is thus established for example that the sample is moved between two temporally adjacent camera images by 5 pixels with respect to its image so that a corresponding displacement of the temporally adjacent camera images can be effected in order to compensate for the sample movement).

A further camera-based system construction according to the invention for the illumination unit and the detection unit uses an LED illumination in which the individual LED illumination elements which emit light of one wavelength are disposed such that, for each image point or for each imaged surface element, the same reflection condition is given over the entire sample surface to be scanned (total camera image). This can be achieved by different angles of inclination of the individual LED elements in a strip, by means of an arrangement of these elements on a bent plate or in the case of a planar arrangement of the LED elements by means of an attachment lens system.

By means of the bent plate or the attachment lens system, in particular effects of the e.g. funnel-shaped camera opening can be compensated for (which would otherwise prevent exact detection and evaluation): because of the corresponding bent plate or attachment lens system, the camera then no longer has a telecentric beam path but rather a fan-shaped one which leads to the fact that actually the same reflection conditions are given for each image point over the entire sample surface to be scanned.

Within the scope of the scope of the present invention, it is also possible to provide the illumination unit which is used with means for changing and/or adjusting the polarisation of the illumination (for example LC element, as used in LC displays). The illumination of the sample can then be effected, as in the case of the "flashing" described earlier, in succession with different polarisation states. For each illumination-polarisation state, different polarisation components for the reflection elements can then, as described earlier, be detected and evaluated.

As an alternative to switching on and off or illumination of the sample by "flashing", also suitable polarisers which produce the desired polarisation states can hence be placed in front of the illumination unit (or in the beam path between illumination unit and sample).

Figure 6:
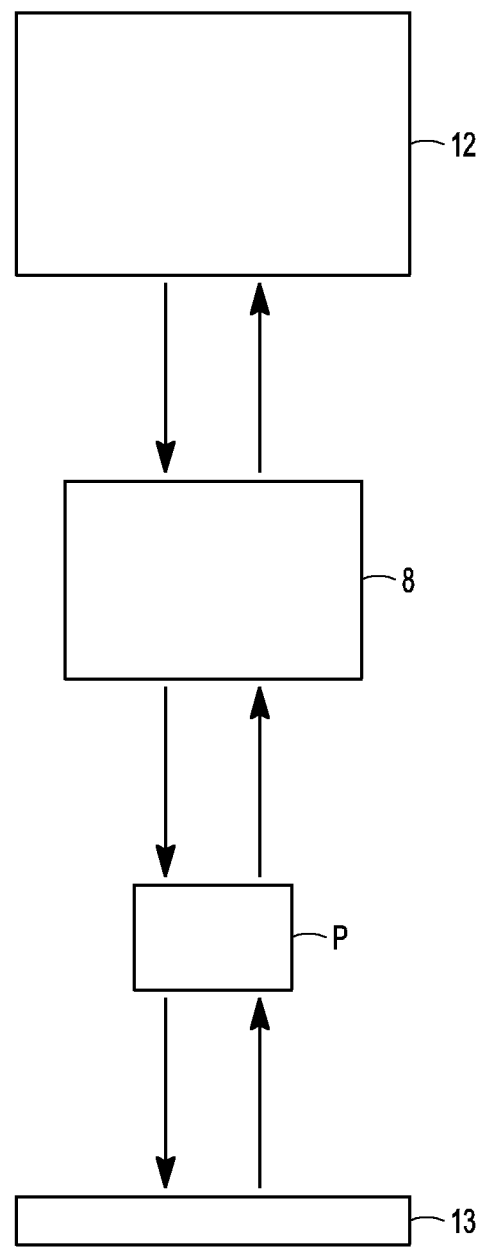

It is also possible to use the illumination unit and the detection unit together with a polarisation-obtaining retroreflector. A flow diagram of such an illustration is provided in FIG. 6. In the case of a laser used in the form of a laser scanner as illumination unit and in the case of a receiver configured suitably as associated detection unit (which can have in particular a polarisation-obtaining beam splitter for dividing the incident laser light into two partial beam paths and also polarising optical elements in these partial beam paths), the illumination unit and the detection unit can also be configured as integrated transmitting and receiving unit 11. A retroreflector 13 must then be provided, the combined transmitting and receiving unit and the retroreflector being configured and disposed as follows: in the combined transmitting and receiving unit 11, transmitting and receiving beam path are coupled via a beam splitter 8 on the same axis. The transmitter illuminates the sample P, the beam components which are reflected by the sample P (i.e. scattered, diffusely reflected or reflectively reflected) are reflected back on the retroreflector 13 per se and arrive at the combined transmitting and receiving unit 12, preferably via the sample P, and there, via the beam splitter 8, at the receiver beam path of the receiver of this combined transmitting and receiving unit. FIG. 6 is a flow diagram and does not illustrate angles of transmitted or reflected light.

With a corresponding arrangement of a laser, which has a non-integrated configuration, and of a receiver which is suitably configured and orientated to receive the reflected light of the laser, the retroreflector is disposed in the above-described case wherever the receiver stands. This has the advantage that if the beams components arrive at the combined transmitting and receiving unit via the object, the radiation is reflected twice on the sample or on the object. Hence improved imaging of the sample or of the object with an improved intensity ratio is effected (if for example in the case of a single reflection on the sample, an intensity ratio of 1:1,000 is present, then the intensity ratio with this construction is 1:1,000$^2$). By means of suitable retroreflectors or adjustment of the back-reflection, in addition a very compact construction can be produced. Finally, within the scope of the devices for optical characterisation as described above and according to the invention, it is also possible (and in particular in the above-described retroreflector variant) to use a laser which scans the sample in lines or in a grid shape as illumination unit (laser scanner system). The detection unit then comprises a receiver, which is suitable for receiving the laser light reflected by the sample, with one or more optical element(s) for separation of the received laser light according to the different polarisation components. In the receiver, a plurality of receiving elements are configured, the number of which corresponds to the number of partial beams resulting from the separation. The evaluation unit can establish, for example by testing the received total intensity, whether surface elements are reflection elements of the sample, i.e. fulfil the reflection condition. The evaluation unit of the above-described devices for optical characterisation according to the invention is configured such that, with it, the reflection elements of the sample can be identified (for example by evaluation of the total intensity received by each object point as a criterion for whether the corresponding object point fulfils the reflection condition, i.e. has the orientation of its surface which is required for further evaluation). The reflection elements are then evaluated further by the evaluation unit for optical characterisation of the sample, i.e. one or more processing step(s) is/are provided in order to implement an overall characterisation of the sample by evaluation of the significant surface elements or of the reflection elements. In order to detect further sample—and/or material parameters of the sample within the scope of this overall characterisation, in addition, delay elements (e.g. $\lambda/4$ plates) can be provided in front of the illumination. It is also possible to use further beam splitters or filters in front of the detection unit or the light-sensitive surface thereof. The orientation, adjustment and arrangement of such delay elements and/or beam splitters or filters can be effected such that determination of further Stokes' parameters is possible. In particular also a monochromatic coherent illumination unit (laser) can be provided so that, due to physical secondary conditions known to the person skilled in the art, merely three Stokes' parameters are required instead of four Stokes' parameters for complete characterisation of the polarisation state of the light reflected by the sample.

According to the invention, systems with angles of incidence and reflection between the two special cases 0° and 180° are possible: in the boundary case of 90°, the sample should hereby be placed between illumination unit and detector. In the special case of 90° and when using a combined illumination—and detection unit or transmitting and receiving unit, the retroreflector is situated behind the sample. In the special case of a 90° arrangement, this involves a polarimetry construction for the optical characterisation of transparent objects. In this case also, in comparison with arrangements according to the state of the art, the advantage is gained that a significantly faster evaluation can be effected: by means of a complete characterisation of the polarisation state, the variation in the illumination conditions required with devices according to the state of the art can be dispensed with. As a result, a test in step with the production of goods is possible for the first time. Just as in the case of the reflection evaluation, a test of the overall intensity is sensible in this case in order to find the object points or surface elements which are relevant for characterisation of the sample. However, in this case, these points are not reflection elements but transmission elements. In this case, the light components reflected by the sample can therefore also concern components transmitted through the sample (transmission instead of reflection or also both components: transmission and reflection). The device can therefore also be configured as transmission system or transmission-reflection system. In a further embodiment, the device according to the invention for optical characterisation comprises the following elements: a laser orientated for one- or two-dimensional scanning with incident light of a sample spatial portion in which the sample can be introduced (illumination unit). For receiving the light reflected through the sample, a receiver which is suitable for receiving laser light is provided as detection unit. This receiver comprises a first, preferably polarisation-obtaining beam splitter for dividing the laser light incident on the receiver into a first and a second partial beam path. In each of these two partial beam paths, a polarising optical element (e.g. polarising prism or polarising beam splitter) is provided, with which the light of the respective partial beam path can be split into two different polarisation components. In the beam path of each of the two thus separated polarisation components, respectively one receiving element is provided, with which the respective polarisation component can be detected (hence in total four receiving elements are provided, two in each of the above-described partial beam paths). A polarisation-changing element is provided merely in one of the two partial beam paths in addition after the beam splitter and in front of the polarising optical element, with which polarisation-changing element the polarisation of this partial beam path can be changed. This changing element can concern in particular a delay plate which is configured preferably as λ/4 plate. The evaluation unit of the device is configured such that, with it, on the basis of the different polarisation components detected by the plurality of receiving elements of the receiver, the polarisation state of the light reflected by the sample can be determined completely for the optical characterisation of the same.

For this purpose, in particular the beam splitter, the polarising optical elements, the changing element and the four receiving elements can be configured, disposed and adjusted such that three or four Stokes' parameters of the reflected light can be calculated from the detected different polarisation components. Since the incident laser light is completely polarised, determination of three of the four Stokes' parameters suffices to calculate the fourth Stokes' parameter (using a secondary condition for monochromatic, coherent light) and hence to characterise completely the polarisation state of the reflected light. With the help of the polarisation state of the reflected light, which is thus determined completely, for example different materials of different sample elements of a bulk material sample can then be identified and differentiated.

The present invention is described subsequently in detail with reference to several embodiments.

There are thereby shown:

FIG. 1 a first embodiment of a device according to the invention using an individual illumination element as illumination unit.

Figure 2:
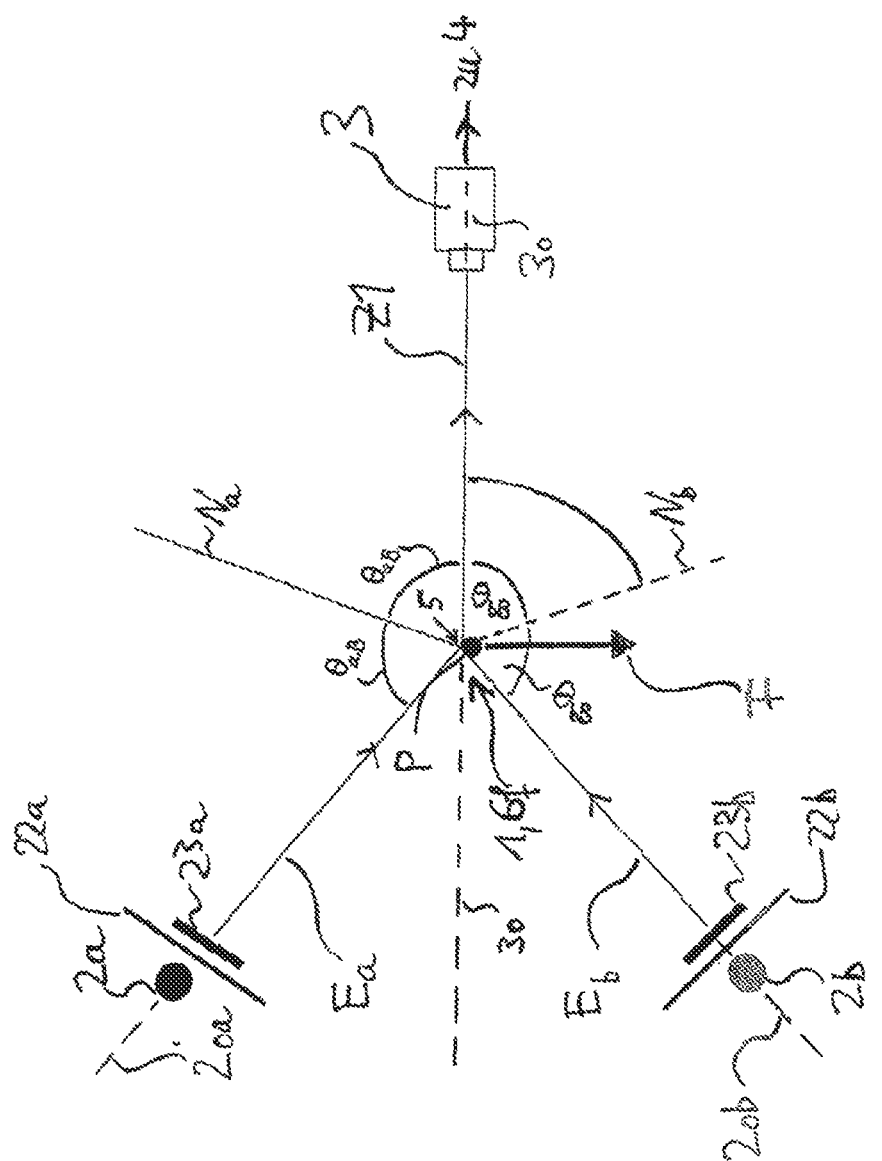

FIG. 2 a further embodiment of the invention in which the illumination unit consists of two separate illumination elements.

FIGS. 3a to 3d examples of identification of a defined material in a bulk material flow of different materials.

Figure 4:
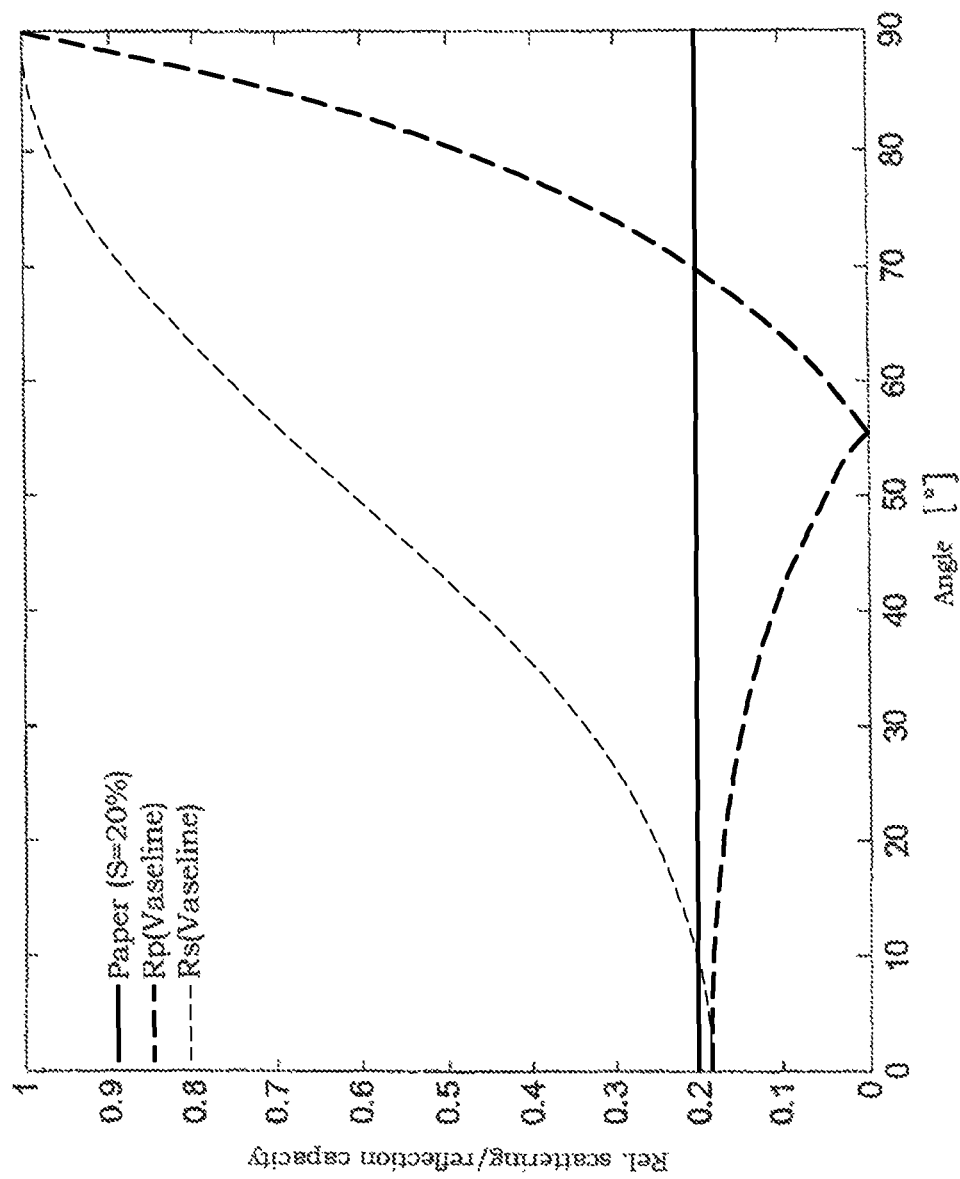

FIG. 4 an example of a device according to the invention configured as testing system for coatings.

Figure 5:
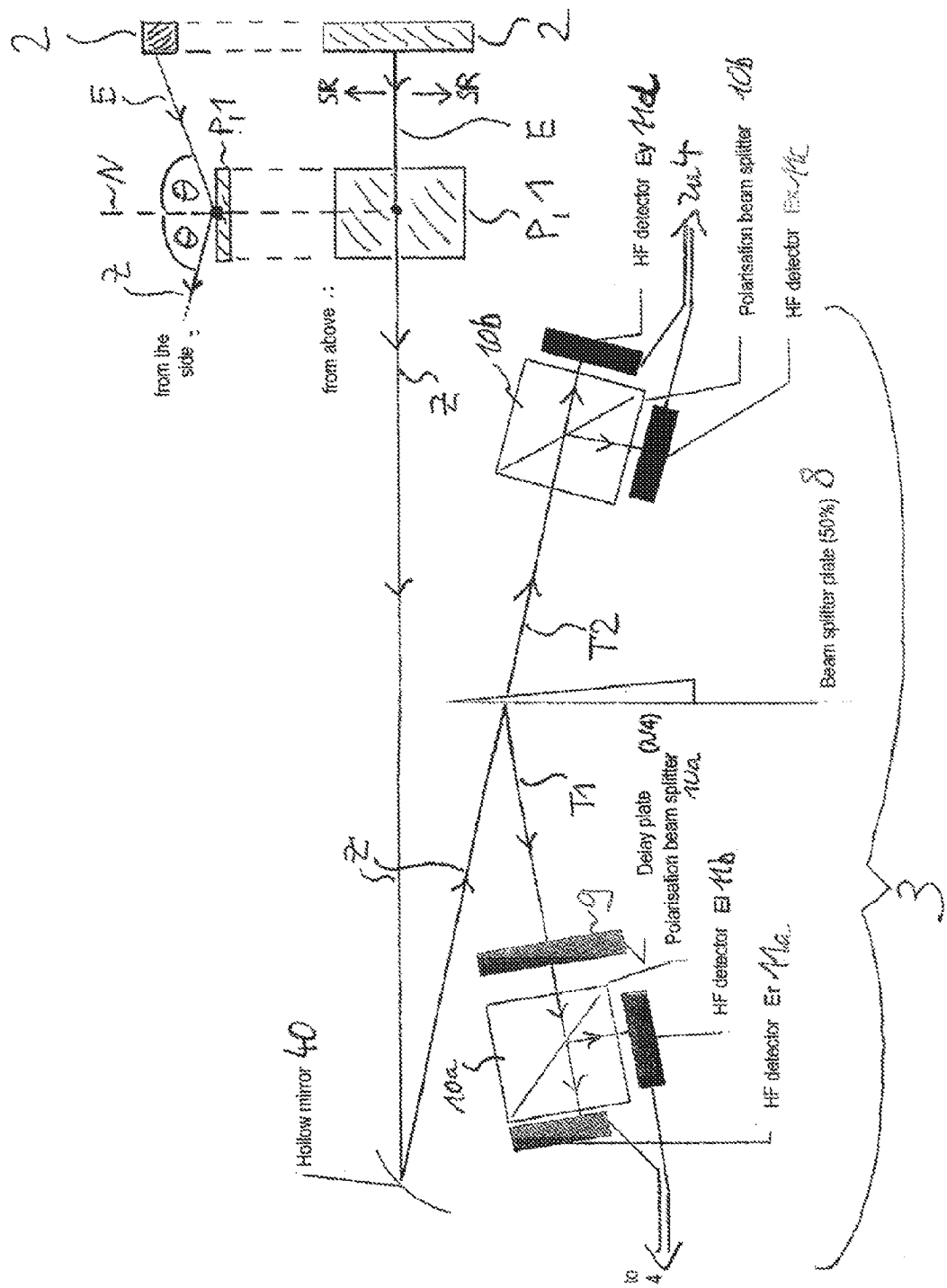

FIG. 5 a further embodiment of the invention which is configured for complete characterisation of the polarisation state of the reflected light.

FIG. 6 a diagram of a device with a retroreflector and a transmitting and receiving unit.

FIG. 1a) shows a device according to the invention which is configured for characterisation of individual sample elements or test pieces P in the form of a bulk material sorting system. The individual objects of the bulk material flow or of the sample P are transported on a planar conveyer belt 30, the outer surface of which, on which the elements of the sample P come to be situated, is white. This serves for better identification of the individual sample elements in the image (see subsequently). The conveyer belt 30 is actuated by two rollers 31, 32; transport of the sample elements P is effected here to the right in the image (arrows); further elements of the bulk material sorting device (e.g. blowing units or collection containers for the sample elements of different material) are not shown here.

The illumination unit 2 of the illustrated device comprises a monochromatic light source 21 which is configured here as LED strip and emits in the green range (550 nm). A diffuser 22 which reduces the modelling of the LED structure 21 is disposed in the beam path after the light source 21. In the beam path behind light source 21 and diffuser 22, the illumination unit 2 has in addition also a polariser 23. The optical axis of the illumination unit 2 consisting of the elements 21, 22 and 23 is characterised here with the reference number 2o. The light E incident on the sample P along the optical axis 2o of the illumination unit 2 is incident at an angle $\theta_B$ (relative to the normal N to the surface of the conveyer belt 30 covered with the individual sample elements) onto the surface of the sample spatial portion 1 which here comprises a defined surface segment parallel to the longitudinal direction of the conveyer belt 30. The corresponding conveyer belt portion is provided here with the reference number 7.

The detection unit 3 of the illustrated system is disposed, relative to the conveyer belt 30, in the same half-space as the illumination unit 2 (i.e. in the half-space situated above the conveyer belt 30) but, viewed relative to the conveyer belt portion 7 or to the sample spatial portion 1 illuminated by the illumination unit 2, is disposed in this half-space on the side situated opposite the illumination unit 2. The optical axis of the detection unit 3 configured as polarisation camera is described here with the reference number 3o.

The illumination unit 2 or the optical axis 2o thereof, the centre of the sample spatial portion 1 or of the illuminated conveyer belt portion 7 and the detection unit 3 or the optical axis 3o of the same, form an isosceles triangle, the longitudinal side of which is formed by the connection line light source 2—detection unit 3 and the cathetus of which is formed by the connection lines light source 2—sample spatial portion 1, 7 and sample spatial portion 1, 7—detection unit 3 (reflection arrangement). The normal N of the longitudinal side of this triangle or the normal to the conveyer belt surface hence bisects the angle between the two optical axes 2o and 3o into two angles $\theta_B$ of equal size, here $\theta_B$=63° applying.

An evaluation unit 4 in the form of a personal computer with suitably configured evaluation programs is connected to the detection unit 3 via a bidirectional data line.

The mode of operation of the device illustrated in FIG. 1a) is described subsequently.

The device is adjusted to differentiate sample elements made of zirconium from sample elements made of glass. For this purpose, the angle $\theta_B$=63° was adjusted to the Brewster angle of the material zirconium. The evaluation or the optical characterisation is now based on the idea that the surface portions of the individual sample elements, which are orientated towards the illumination unit-detection unit half-space, can constantly be differentiated, that there is hence (cf. FIG. 1b) at least one surface element for each sample element P, the normal of which surface element is orientated parallel to the normal N or to the angle bisector of the two optical axes 2o, 3o. For such a surface element of a sample element P, the incident radiation E hence impinges on the surface of the sample element P precisely at the Brewster angle $\theta_B$ of zirconium.

FIG. 1b) illustrates how those surface elements, for which this reflection condition is fulfilled and which are therefore reflection elements 5 of the sample elements P, can be differentiated from other imaged surface elements of the sample or from imaged surface elements of the background or of the conveyer belt surface (these surface elements are subsequently described in summary as scattered elements 6 although the physical process underlying their imaging can also be a process other than a scattering process): if in fact (relative to the overall reflected light radiation Z) not only does a reflected beam component Z1 arrive at the detection unit 3 from reflection elements 5 of the sample P and lead there to imaging of the corresponding surface element by the detection unit 3, but also light Z2 which is scattered for example on a scattering element 6 likewise arrives at the detector 3 (in FIG. 1b), this is for example light which has been reflected already once on the surface of the conveyer belt 30 and is therefore incident, from a direction of incidence E2 which does not coincide with the optical axis 2o, onto the scattering element 6 of the surface of the sample P, which light is then scattered in the direction Z2=Z1 into the polarisation camera 3). However scattered light from scattering elements 6 can be differentiated from reflected light from reflection elements 5 by evaluation of the intensity of a polarisation component recorded by the polarisation camera 3 (see subsequently) or also by evaluation of the incident overall intensities of all detected polarisation components. Thus the reflection elements 5 effect for example a significantly higher overall intensity which impinges on the corresponding image element of the polarisation camera 3 than the scattering elements 6. The two types 5, 6 of surface elements can therefore be differentiated by setting a predetermined threshold value (which can be determined for example from an average intensity over the entire image). Surface elements 5 which fulfil the reflection condition are therefore particularly bright in the imaging. These surface elements 5 alone are then evaluated further for characterisation of the sample P or the individual sample elements thereof.

In order to ensure that the specific reflection elements 5 in fact also concern imaged surface elements of sample elements P (and not for example light components reflected on the white background or on the surface of the conveyer belt 30), in addition the position of the potential candidates for reflection elements 5 can be evaluated in the total recorded image: by means of image processing algorithms for edge detection, known to the person skilled in the art (search for closed curves in the image which is differentiated once or twice and threshold value-treated), the position, the size and the shape of the individual sample elements of the sample P can be established for example. Reflection elements R can then be merely those surface elements or points in the image which come to be situated inside the image of a sample element or inside such closed curves. In order to determine the reflection elements 5, a combination of intensity—and position evaluations can therefore be used (only particularly bright surface elements in the central region of the imaging of a bulk material object P can hence be reflection elements 5 in the system of FIG. 1).

Further evaluation of the identified reflection elements 5 in the image of the camera 3 and the sample material characterisation based thereon then takes place as follows: the polarisation camera 3 is configured for separation of two orthogonal polarisation components, namely of the polarisation component of light E which is incident parallel to the plane of incidence of the reflection elements 5 (plane parallel to the conveyer belt surface) and of the polarisation component incident perpendicular thereto. If an imaged sample element P concerns an element made of zirconium, then, since here the Brewster condition is fulfilled, merely light polarised parallel to the above-described plane is reflected. Only this polarisation component can hence be detected for zirconium sample elements P with one channel of the camera 3, whilst the other channel of the camera 3 (which is configured for detecting light polarised perpendicular thereto) can detect no reflected light. If the observed sample element P concerns an element made of a material other than zirconium, then light of both polarisation components is detected by the polarisation camera 3 (i.e. both channels of the camera are affected). If the ratio of the intensities of both polarisation components in both channels or images of the sample spatial portion 1, recorded by the polarisation camera 3, is hence formed for all those surface elements which are reflection elements 5, then this ratio varies significantly for reflection elements of zirconium surfaces and for reflection elements of surfaces of other materials. By setting a suitable threshold value, zirconium sample elements can hence be differentiated from other sample elements.

If light which is polarised for example parallel to the plane of incidence is displayed by the polarisation camera in blue and light polarised perpendicular thereto in red, then this means that, in the images recorded and superimposed by the polarisation camera, the reflection elements of zirconium sample elements P appear to be purely blue.

Figure 3A:
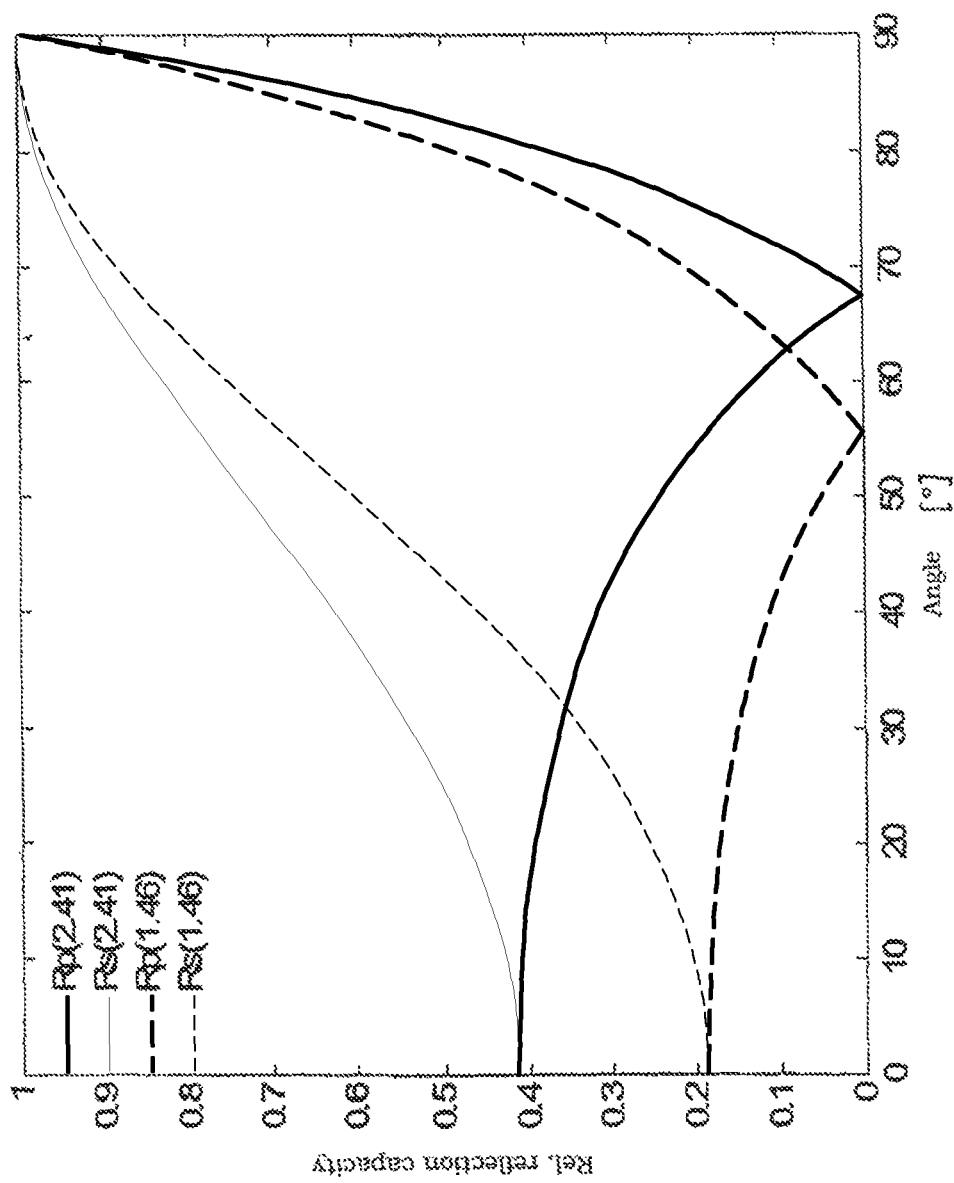
Figure 3B:
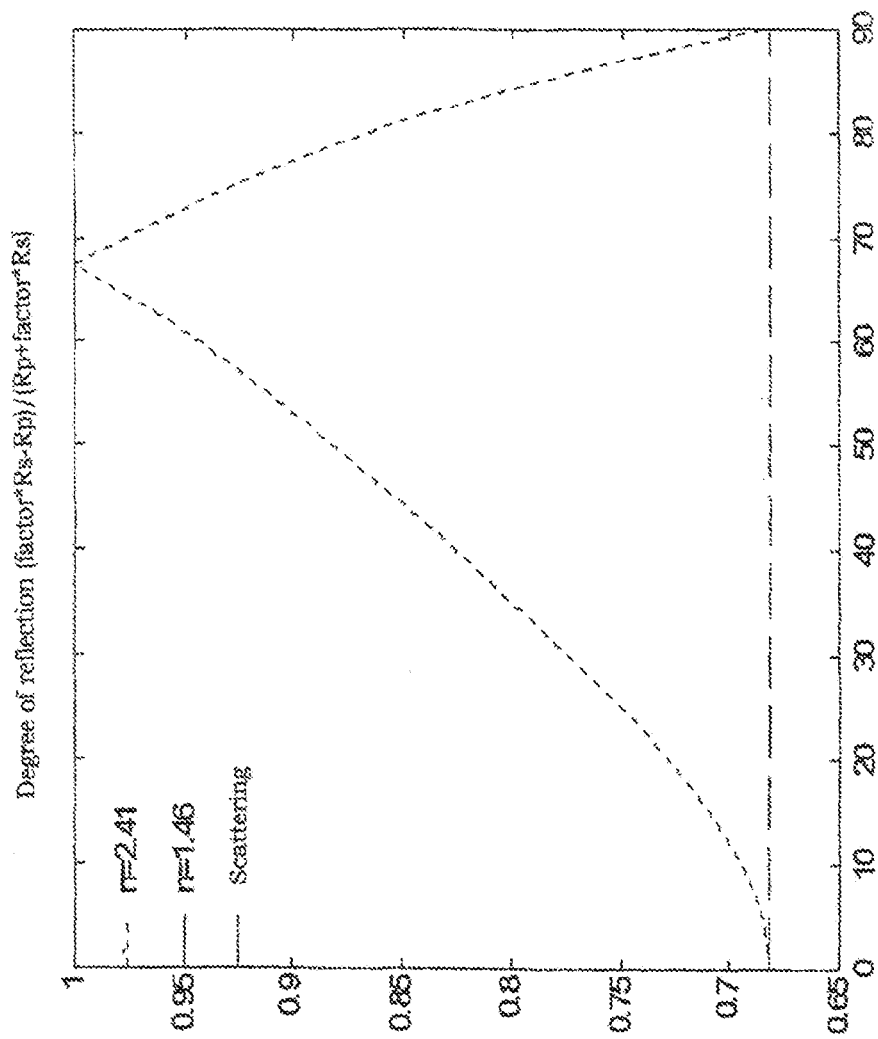
Figure 3C:
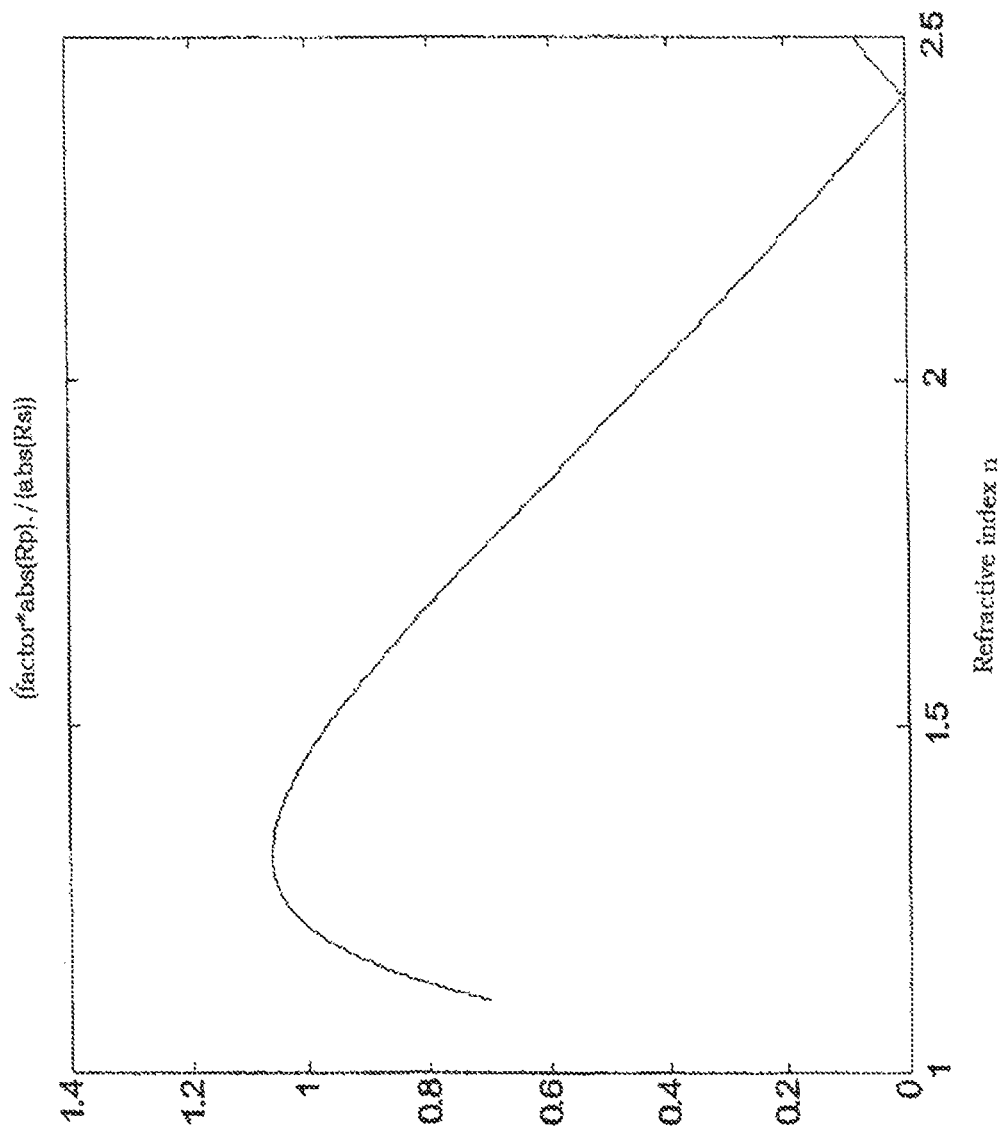
Figure 3D:
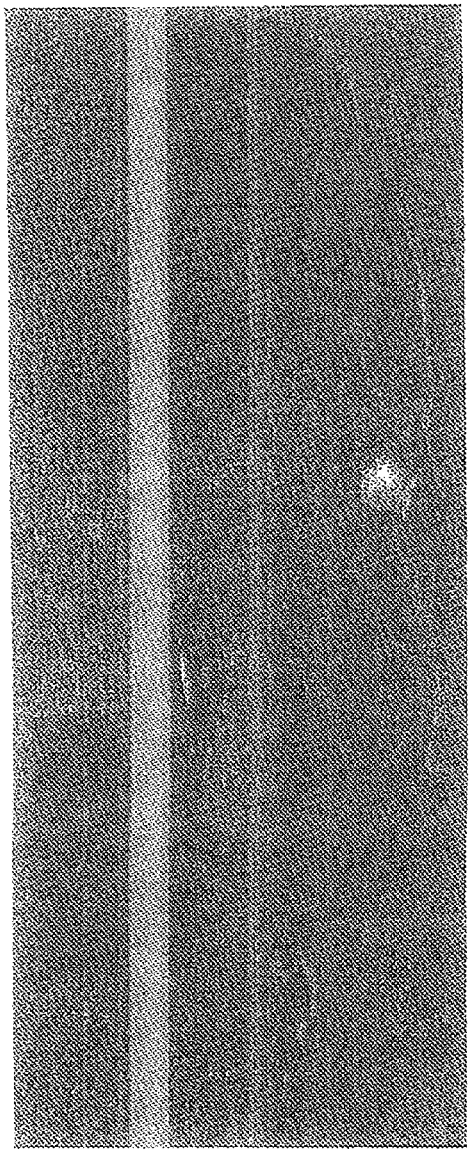
Figure 3D:
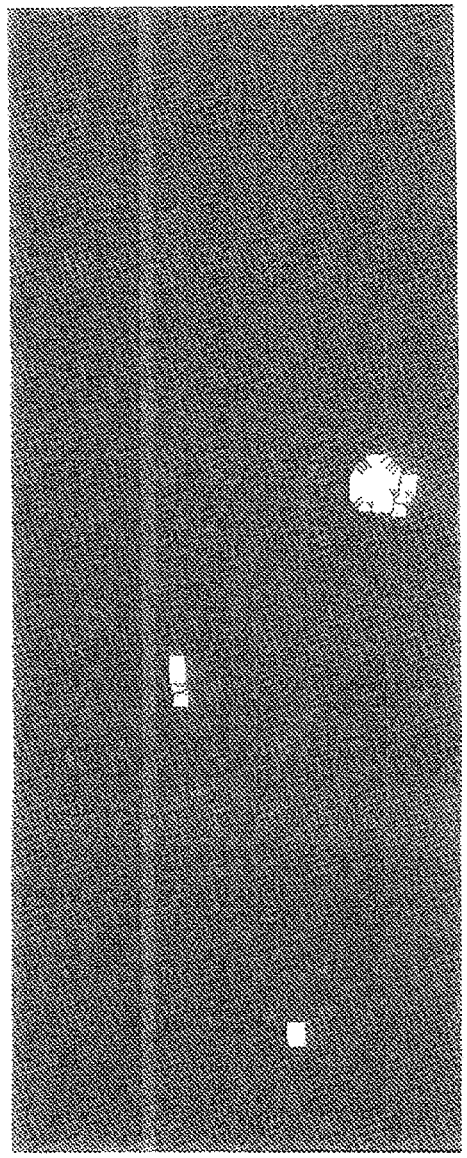

FIGS. 3a to 3d show examples of the differentiation of diamond and quartz glass (FIGS. 3a to 3c) and of zirconium crystals in a bulk material flow P of such crystals, of glass shards and of metal rings (FIG. 3d). The polariser 23 was adjusted for FIG. 3d such that the conveyer belt surface (background) reflects both polarisation directions with the same intensities in the direction of the polarisation camera 3. $\theta_B$ is thereby 63° (Brewster angle for zirconium). Even if the sample elements P conveyed through the sample spatial portion 1 have an irregular geometry and their precise position is unknown, nevertheless an object characterisation is possible since the individual sample elements have differentiatable surfaces, i.e. each bulk material particle has at least one surface element which fulfils the reflection condition (angle of incidence=$\theta_B$). Since reflection provides very much stronger signals than scattering, these surface elements can be identified. The underlying physical principles of this reflectometry (reflection of polarised light on the medium, Fresnel formulae for perpendicular and for parallel polarisation and also the law of refraction) are known to the person skilled in the art.

FIG. 3a shows how a sorting criterion can be developed from the Fresnel formulae by calculation of curves for the relative reflection capacity of two different materials: FIG. 3a shows the reflection capacity as a function of the angle of incidence for the materials quartz (refractive index=1.46) and diamond (refractive index=2.41), i.e. in the case where differentiation of diamond from quartz glass is desired. The Figure clearly shows the different Brewster angles for the two materials; for separation of the two materials, an arrangement at the Brewster angle $\theta_B$ of the sought material can hence be effected (i.e. for diamond at $\theta_B$=67.5°). Those reflection elements 5 in which merely one polarisation component remains after reflection can then be determined. $R_S$ is the reflection capacity for light polarised perpendicular to the plane of incidence and $R_P$ is the reflection capacity for light polarised parallel to the plane of incidence.

An increase in sensitivity for separation of the two materials can be effected by adaptation of the illumination. For example in an arrangement for differentiating zirconium ($\theta_B$=63°), the illumination can be adjusted by means of the polariser 23 such that the two reflected intensities are the same for the extraneous material (for example glass or metal). This adjustment can be effected by means of the polariser 23 such that then an extraneous material sample is brought into the measuring field and subsequently the position of the polariser is changed thus until both intensities are the same.

FIG. 3*b* shows again, for the example of diamond/quartz glass, the degree of reflection, likewise (cf. FIG. 3*a*) as a function of the angle of incidence $\theta$.

In the case of an arrangement in which the Brewster angle $\theta_B$ of diamond is chosen as angle of incidence, the characteristic line shown in FIG. 3*c* is finally produced for the optical differentiation of diamond and of materials with a deviating refractive index (e.g. quartz glass). For the illustrated example, the polarisation of the illumination was adjusted such that not reflecting, but scattering particles or surface elements with $R_P$=$R_S$ have a quotient of 5. Hence a sorting criterion which falls monotonically within a wide range with the refractive index n is produced.

When adjusting the system for identification of zirconium, the ratio between blue and red channel is then highest on the surface elements 5 of the zirconium crystals which are orientated parallel to the conveyer belt surface and fulfil the reflection condition. The ratio can hence be used for the purpose of identifying the zirconium crystals in the individual sample elements of the bulk material flow.

FIG. 3*d* shows a corresponding result, in which, for formation of the ratio, the blue channel B has been divided by the sum of both channels R+B (R=red channel intensity). After setting the threshold value (FIG. 3*d* on the right), it can be readily detected that zirconium crystals are marked in image 3. The glass shards (further irregular elements in FIG. 3*d* on the left) and a metal ring present in the bulk material flow (FIG. 3*d* on the left at the top) remain dark, i.e. are not identified.

FIG. 4 illustrates a further test task which can be achieved with the device according to the invention shown in FIG. 1: paper/gauze is coated with Vaseline during production. What is sought is a test system which automatically tests the entire coating during production. The approach for the solution according to FIG. 1 is based here on reflectometry, the laminate sample P which is flat here being disposed at the Brewster angle $\theta_B$ of 55.5° for Vaseline. The curves calculated from the Fresnel formulae for the reflection capacity of Vaseline are shown in FIG. 4. By way of comparison, the expected course of a paper scattering homogeneously with 20% is plotted. Here also, the separation of the two mentioned materials can be implemented again by evaluation of the two channels of the polarisation camera 3 (test on $R_S$=0, i.e. for the presence only of reflected light polarised parallel to the interface). The result of the test is the information as to whether paper is coated with Vaseline or not. Paper surfaces coated with Vaseline are hence distinguished by an intensely blue colour, merely the blue channel of the polarisation camera 3 responds. The degree of polarisation of the imaged surface elements can hence be calculated from the intensities B of the blue channel and from the intensities R of the red channel as follows: B/(B+R). Vaseline-coated surface components hence produce the value B/(B+R)=1. For production control, for example the coated surface component on the total surface component can be evaluated.

FIG. 2 shows a further device according to the invention in which a plurality of individual illumination elements 2*a*, 2*b*, as illumination unit 2, are used in the form of monochromatic light sources with emission wavelengths of respectively $\lambda$=550 nm. Viewed in the direction of incidence, a diffuser 22*a*, 22*b* and a polariser 23*a*, 23*b* are disposed behind each illumination element 2*a*, 2*b*, similarly as shown in FIG. 1. The detection unit 3 and the evaluation unit 4 (not shown here) are configured similarly to the case described in FIG. 1 (differences see below). The illustrated device is configured as bulk material sorting device in which the bulk material (of which only a single sample element P is shown here) traverses a sample spatial portion 1 in the form of a free falling stretch part 6*f* below a vibrator (not shown). The optical axis 3*o* of the polarisation camera 3 is situated here in a horizontal plane perpendicular to the falling direction F of the sample elements P. In each of the half-spaces configured on both sides of this horizontal plane, an illumination element 2*a*, 2*b* (together with associated diffuser 22*a*, 22*b* and polariser 23*a*, 23*b*) is disposed respectively. The angle between the two optical axes 2*oa* and 2*ob* of the two illumination elements 2*a*, 2*b* and of the above-described horizontal plane is respectively the same, the illumination elements 2*a*, 2*b* and the camera 3 are thereby disposed such that their optical axes 2*oa*, 2*ob* and 3*o* are situated in a plane perpendicular to the above-described horizontal plane.

Due to this arrangement, the reflection condition for the two illumination elements respectively is hence the same: the angle bisector $N_a$ divides the angle spanned by the two optical axes 2*oa* and 3*o* or the angle spanned by the direction of incidence Ea of the upper illumination element 2*a* and of the reflection direction Z1 into two angles $\theta_{aB}$ of equal size, which are configured corresponding to the Brewster angle $\theta_B$ of a material to be identified in the sample flow P. The angle bisector $N_b$ likewise divides the angle spanned by the optical axis 2*ob* of the lower illumination element 2*b* (i.e. the incident light $E_b$) and the optical axis 3*o* of the polarisation camera 3 (or the corresponding reflected imaged light component Z1) into two angle portions $\theta_{bB}$ of equal size. Due to the above-described arrangement, there applies here $\theta_{aB}$=$\theta_{bB}$. Both illumination elements 2*a* and 2*b* are hence adjusted to one and the same angle, the Brewster angle of the material to be identified.

Identification of the reflection elements 5 and the subsequent evaluation of the polarisation components for these reflection elements for optical characterisation of the sample elements P is now effected analogously to the case described for FIG. 1. However the reflection condition for the partial system consisting of the illumination unit 2*a* and the camera 3 is fulfilled at a different, later point in time than for the further partial system consisting of the illumination element 2*b* and the camera 3: if a sample element P falls through the illustrated falling stretch F, then surface elements situated on the rear-side thereof (in the image: side situated at the top) fulfil the reflection condition, i.e. are reflection elements 5 when the observed sample element P is disposed, with its rear-side, exactly at the height of the horizontal plane of the optical axis 3*o*, this horizontal plane is therefore precisely the tangential plane to the rear-side of the sample element P. For the system 2*b*, 3, the reflection condition is in contrast already fulfilled at a point in time preceding this point in time, namely when the front-side of the falling sample element P (the side situated at the bottom in the image) impacts precisely from above on the horizontal plane of the optical axis 3*o*, this horizontal plane abuts therefore tangentially at the front-side of the sample element P.

The significant surface elements of the sample P which are potentially possible as reflection elements 5 must hence be situated in the images recorded currently by the camera 3*o* initially on the front-side and then on the rear-side of the imaged object (which can be identified again by for example gradient-based image processing mechanisms with the aid of its outline). In this respect, the conditions for identification of the reflection elements 5 differ from those of the system shown in FIG. 1 in which the reflection elements 5 must be situated for instance in the centre of the images of the individual identified sample elements. Apart from the above-described differences during identification of the reflection elements 5, evaluation of the different polarisation components for the identified reflection elements can however be effected for optical characterisation of the sample P entirely analogously to the case described for FIG. 1.

Analogously to the case shown in FIG. 2, an illumination unit which comprises, instead of two illumination elements 2a, 2b, in total four illumination elements which are disposed in a plane perpendicular to the optical axis 3o and equidistantly on a circle about this optical axis 3o (angle spacings of the individual illumination elements 90°) can also be used. Similarly to the case shown in FIG. 2, illumination is then effected such that surface elements on the edge of the objects P are examined from four directions on the basis of intensity as to whether they have matching surface normals N. Hence characterisation of the falling sample elements P of the bulk material flow with up to four points is possible.

For the objects in FIG. 2, it can hence be tested whether there are surface elements or points with a pure colour, e.g. blue (cf. description for FIG. 1: then merely one of the two polarisation components is present) and whether these points are situated on the front- or rear-side of the respective sample elements P (relative to the direction of movement F).

With corresponding adjustment to the Brewster angle and in the case of four individual illumination elements at a 90° spacing (not shown), objects made of the material to be identified are characterised according to the Brewster angle $\theta_{aB}=\theta_{bB}$, for example by blue image elements at a second, later point in time (scanning of the front), red image elements at a first later point in time (scanning of the left and of the right side) and by further blue image elements at a third, still later point in time (scanning of the rear).

FIG. 5 shows finally a further device according to the invention for the optical characterisation of a planar, laminate sample P in a sample spatial portion 1 on the basis of a laser scanner system. The laser 2 as illumination unit, which scans, one-dimensionally, the sample spatial portion 1 in the direction SR perpendicular to the direction of incidence E of the light, beams light at the angle of incidence θ (angle between the sample normal N and the direction of incidence E of the laser light) onto the sample surface of the sample P. Cf. in this respect FIG. 5 on the right at the top which shows a section perpendicularly through the irradiated sample surface and FIG. 5 in the centre at the right which shows a plan view on the irradiated sample surface, i.e. a view in the direction of the normal N. The light Z reflected at the corresponding angle of reflection θ (reflection law) is conducted for evaluation to the receiver 3 shown on the left and centre in FIG. 5.

The device shown in FIG. 5 is based on the observation that the emission laser 2 of the illustrated scanner emits monochromatic, coherent radiation so that the radiation E received by the sample is already completely polarised. In this case, the detection of three Stokes' parameters from the reflected laser light components Z hence suffices for complete characterisation of the polarisation state of the reflected or detected light radiation Z.

Viewed in the irradiation direction of the reflected light component Z, the illustrated receiver 3 now comprises in succession in the beam path the following components:

A hollow mirror 40 configured for focusing the light component Z reflected on the sample surface P towards a beam splitter plate 8.

The polarisation-obtaining beam splitter plate 8 with which respectively 50% of the incident, reflected radiation Z is divided into a first partial beam path T1 and into a second partial beam path T2.

In the first partial beam path T1: firstly a delay plate (λ/4 plate) 9 which directs the light of the first partial beam path T1 towards a first polarisation beam splitter 10a which is configured for differentiating two polarisation components of the incident light which are orthogonal relative to each other. The first of these two polarisation components is detected with a first receiving element 11a, the other of these two polarisation components with a further receiving element 11b (intensity detectors).

The second partial beam path T2 is basically constructed just like the first partial beam path T1, however the delay plate 9 is omitted here so that, in this partial beam path, merely a second polarisation beam splitter 10b and two further receiving elements 11c and 11d are disposed, with which the two polarisation components which are orthogonal relative to each other can be detected in the second partial beam path T2.

The four receiving elements 11a to 11d are then connected respectively via bidirectional signal lines to an evaluation unit 4 (not shown).

With the illustrated receiver 3, the polarisation state of the reflected radiation Z can hence be characterised completely as follows:

With the help of the receiving elements 11c and 11d of the partial beam path T2, the intensities $I_0$ and $I_{90}$ for two linear polarisation components which are orthogonal relative to each other are determined. The combination of the delay plate 9 and of the splitter 10a produces a beam splitter for splitting the incident light into right-circular and left-circular polarised light. (Intensities $I_{RZ}$ and $I_{LZ}$ for right-circular and for left-circular polarised light). Hence four different polarisation components can be determined.

The four sought Stokes' parameters I, S, U and V can hence be determined from the linear polarisation components (intensities $I_0$ and $I_{90}$) which are detected by the receiving elements 11a to 11d, i.e. orthogonal to each other, and from the circular polarisation components (right-circular polarised component with the intensity $I_{RZ}$ and left-circular polarised component with the intensity $I_{LZ}$) as follows $$I=I_0+I_{90}$$

$$S=I_0-I_{90}$$

$$V=I_{RZ}-I_{LZ},$$

then with the secondary condition for monochromatic coherent laser radiation of $$S+U+V=1$$

the fourth Stokes' parameter $U=I_{45}-I_{135}$ being able to be calculated.

The illustrated device for optical characterisation of FIG. 5 hence enables calculation of the complete polarisation state of the reflected light component Z from the received signal intensities of the four receiving elements 11a to 11d. Since the polarisation state of the reflected light Z depends upon the respectively examined sample material of the sample P, the device shown in FIG. 5 can be used for material characterisation of the sample P.

If receiver beam path and transmitter beam path are produced in the same housing (integrated transmitting and receiving unit), a corresponding characterisation of the material can be effected provided that light reflected on the sample (reflective) impinges on a retroreflector which reflects the beams per se back to the combined transmitting and receiving unit. In contrast to the arrangement with separate transmitter and receiver, the light is however reflected twice on the sample. The polarisation effects on the sample hence influence the received intensities quadratically.

| | | |
|---|---|---|
| Monochromatic light source | Diffuser | Polariser |
| Polarisation camera | Test piece | White background |
| Rel. reflection capacity | Angle | |
| Degree of reflection (factor * Rs − Rp)/ (Rp + factor * Rs) | | Scattering |
| Refractive index n (factor*abs(Rp)./(abs(Rs)) | | |
| Resulting image (blue channel divided by sum of blue channel and red channel) | | |
| Threshold 181, thick 8 | | |
| Paper (S = 20%) | | |
| Paper (S = 20%) | | |
| Rp(Vaseline) | | |
| Rs(Vaseline) | Angle | |
| Rel. scattering/ reflection capacity | | |
| Hollow mirror | from the side | |
| from above | HF detector | Polarisation beam splitter 10b |
| HF detector | Delayplate | |
| Polarisation beam splitter to | HF detector | |
| 4 | Beam splitter plate (50%) | |

The invention claimed is:

1. A device for optical characterisation of a sample and/or of the materials of the sample, the device comprising:
a laser as illumination unit or part of the same which is capable of being orientated for one- or two-dimensional scanning with incident light of a sample spatial portion into which the sample can be introduced,
a receiver as detection unit or part of the same which is capable of being orientated to receive light which is reflected by a sample introduced into the sample spatial portion,
the receiver comprising:
a first beam splitter, which is polarization-maintaining, for the light reflected by the sample, for dividing the laser light incident on the receiver into a first and a second partial beam path,
respectively in the first and in the second partial beam path:
a polarising optical element with which the light of the respective partial beam path can be split into two different polarisation components, a receiving element respectively for detecting light of the respective polarisation component being disposed in the beam path of each of the two thus separated polarisation components, and
a polarisation-changing element merely in one of the two partial beam paths after the first beam splitter and in front of the polarising optical element, with which polarisation-changing element the polarisation of the light of this partial beam path is capable of being changed, and
an evaluation unit with which, on the basis of the different polarisation components detected by the receiving elements of the receiver, the polarisation state of the light reflected by the sample is determined for the optical characterization,
wherein the illumination unit comprising the laser and the detection unit comprising the receiver are configured integrated as transmitting and receiving unit, and
wherein the device comprises a retroreflector as follows:
the laser and the receiver of the transmitting and receiving unit and also the retroreflector are disposed and orientated such that a sample introduced into the sample spatial portion is illuminated by the laser and in that laser light beam components which are scattered, diffusely reflected, reflectively reflected, or transmitted by the sample, are reflected back by the retroreflector per se such that the laser light beam components are reflected back per se by the retroreflector via the sample and arrive at the transmitting and receiving unit for division there into the first and the second partial beam path through the receiver.

2. The device according to claim 1, wherein the transmitting and receiving unit is configured such that the laser light beam components emanating from the laser and illuminating the sample, on the one hand, and the laser light beam components which have arrived at the transmitting and receiving unit by means of back-reflection, on the other hand, are coupled on the same optical axis.

3. The device according to claim 1, wherein the first beam splitter, the polarising optical elements, the polarisation-changing element and the receiving elements are configured, are disposed, or can be disposed and/or are adjusted or can be adjusted in order to determine three of four Stokes' parameters of the reflected light (Z) from the detected different polarisation components and in that the polarisation state of the light reflected by the sample can be determined from the three thus determined Stokes' parameters using a secondary condition for coherent light.

* * * * *